(12) United States Patent
Giannoukakis et al.

(10) Patent No.: US 10,105,334 B2
(45) Date of Patent: Oct. 23, 2018

(54) PARTICLE FORMULATIONS OF ALL-TRANS RETINOIC ACID AND TRANSFORMING GROWTH FACTOR BETA FOR THE TREATMENT OF TYPE 1 DIABETES MELLITUS

(71) Applicants: University of Pittsburgh—Of the Commonwealth System of Higher Education, Pittsburgh, PA (US); Duquesne University, Pittsburgh, PA (US)

(72) Inventors: Nick Giannoukakis, Coraopolis, PA (US); Massimo M. Trucco, Pittsburgh, PA (US); Wilson S. Meng, Sewickley, PA (US)

(73) Assignees: University of Pittsburgh—Of the Commonwealth System of Higher Education, Pittsburgh, PA (US); Duquesne University, Pittsburgh, PA (US)

( * ) Notice: Subject to any disclaimer, the term of this patent is extended or adjusted under 35 U.S.C. 154(b) by 244 days.

(21) Appl. No.: 15/112,152

(22) PCT Filed: Jan. 16, 2015

(86) PCT No.: PCT/US2015/011837
§ 371 (c)(1),
(2) Date: Jul. 15, 2016

(87) PCT Pub. No.: WO2015/109245
PCT Pub. Date: Jul. 23, 2015

(65) Prior Publication Data
US 2016/0338984 A1    Nov. 24, 2016

Related U.S. Application Data

(60) Provisional application No. 61/928,909, filed on Jan. 17, 2014.

(51) Int. Cl.
| | |
|---|---|
| *A61K 31/203* | (2006.01) |
| *A61K 9/50* | (2006.01) |
| *A61K 38/50* | (2006.01) |
| *A61K 45/06* | (2006.01) |
| *A61K 9/16* | (2006.01) |
| *A61K 47/48* | (2006.01) |
| *A61K 38/18* | (2006.01) |

(52) U.S. Cl.
CPC ............ *A61K 31/203* (2013.01); *A61K 9/167* (2013.01); *A61K 9/5031* (2013.01); *A61K 9/5089* (2013.01); *A61K 38/1841* (2013.01); *A61K 45/06* (2013.01); *A61K 47/48246* (2013.01); *A61K 47/48861* (2013.01)

(58) Field of Classification Search
None
See application file for complete search history.

(56) References Cited

FOREIGN PATENT DOCUMENTS

| EP | 1 707 195 A1 | 10/2006 |
|---|---|---|
| WO | WO 2006/088741 A2 | 2/2006 |
| WO | WO 2012/054920 A3 | 4/2012 |
| WO | WO 2013/112456 A1 | 8/2013 |

OTHER PUBLICATIONS

Capurso et al., "Development of a nanoparticulate formulation of retinoic acid that suppresses Th17 cells and upregulates regulatory T cells," *Self Nonself* 1(4): 335-340 (Oct.-Dec. 2010).
International Search Report from parent PCT Application No. PCT/US2015/011837, 5 pages (dated Mar. 17, 2015).
Kovacs et al., "Characterization of nickel-decorated PLGA particles anchored with a his-tagged polycation," *J. Biomater. Sci. Polym. Ed.* 20(9): 1307-1320 (2009).
Lewis et al., "Combinatorial delivery of immunosuppressive factors to dendritic cells using dual-sized microspheres," *J. Mater. Chem. B. Mater. Biol. Med.* 2(17): 2562-2574 (Dec. 19, 2013).
Sy et al., "Surface functionalization of polyketal microparticles with nitrilotriacetic Acid-nickel complexes for efficient protein capture and delivery," *Biomaterials* 31: 4987-4994 (2010).
Written Opinion from parent PCT Application No. PCT/US2015/011837, 5 pages (dated Mar. 17, 2015).
Almouazen et al., "Development of a nanoparticle-based system for the delivery of retinoic acid into macrophages," *International Journal of Pharmaceutics* 430: 207-215 (2012).
Brisaert et al., "Investigation of the chemical stability of an erythromycin-tretinoin lotion by the use of an optimization system," *International Journal of Pharmaceutics* 197: 153-160 (2000).
Carneiro et al., "Formation of ion pairing as an alternative to improve encapsulation and anticancer activity of all-trans retinoic acid loaded in solid lipid nanoparticles," *International Journal of Nanomedicine* 7: 6011-6020 (2012).
Charoenputtakhun et al., "All-trans retinoic acid-loaded lipid nanoparticles as a transdermal drug delivery carrier," *Pharm. Dev. Technol.* 19(2): 164-172 (2014).
Eichenfield et al., "Tretinoin microsphere gel 0.04% pump for treating acne vulgaris in preadolescents: A randomized, controlled study," *Pediatric Dermatology* 29(5):598-604 (2012).
Keijzer et al., "PLGA nanoparticles enhance the expression of retinaldehyde dehydrogenase enzymes in dendritic cells and induce FoxP3+ T-cells in vitro," *Journal of Controlled Release* 168: 35-40 (2013).
Liang et al., "Dual release of dexamethasone and TGF-β3 from polymeric microspheres for stem cell matrix accumulation in a rat disc degeneration model," *Acta Biomaterialia* 9: 9423-9433 (2013).

(Continued)

*Primary Examiner* — Jeffrey T. Palenik
(74) *Attorney, Agent, or Firm* — Klarquist Sparkman, LLP (57) ABSTRACT

Particle formulations are disclosed that include polymeric particles containing a small molecule drug and a high molecular weight therapeutic protein. Methods of making and using the particle formulations also are disclosed. These particle formulations are of use to treat an autoimmune disease, such as diabetes, or an inflammatory disease.

15 Claims, 3 Drawing Sheets

(56) References Cited

OTHER PUBLICATIONS

Lu et al., "Porous chitosan scaffolds with embedded hyaluronic acid/chitosan/plasmid-DNA nanoparticles encoding TGF-β1 induce DNA controlled release, transfected chondrocytes, and promoted cell proliferation," *PLOS* 8(7): e69950 (13 pages) (Jul. 23, 2013).

Marchiori et al., "Improved tretinoin photostability in a topical nanomedicine replacing original liquid suspension with spray-dried powder with no loss of effectiveness," *Drug Development and Industrial Pharmacy*, 39(4): 579-586 (2013).

Narvekar et al., "A novel hybrid delivery system: Polymer-oil nanostructured carrier for controlled delivery of highly lipophilic drug all-trans-retinoic acid (ATRA)," *International Journal of Pharmaceutics 436*: 721-731 (2012).

Raza et al., "Nano-lipoidal carriers of tretinoin with enhanced percutaneous absorption, photostability, biocompatibility and antipsoriatic activity," *International Journal of Pharmaceutics* 456: 65-72 (2013).

Solorio et al., "Engineered cartilage via self-assembled hMSC sheets with incorporated biodegradable gelatin microspheres releasing transforming growth factor-β1," *J. Control Release.* 158(2): 224-232 (Mar. 10, 2012).

Solorio et al., "Spatiotemporal regulation of chondrogenic differentiation with controlled delivery of transforming growth factor-β1 from gelatin microspheres in mesenchymal stem cell aggregates," *Stem Cells Translational Medicine* 1:632-639 (2012).

Yao et al., "Efficient simultaneous tumor targeting delivery of all-trans retinoid acid and paclitaxel based on hyaluronic acid-based multifunctional nanocarrier," *Mol. Pharmaceutics* 10: 1080-1091 (2013).

PARTICLE FORMULATIONS OF ALL-TRANS RETINOIC ACID AND TRANSFORMING GROWTH FACTOR BETA FOR THE TREATMENT OF TYPE 1 DIABETES MELLITUS

CROSS-REFERENCE TO RELATED APPLICATIONS

This is a § 371 U.S. national stage of International Application No. PCT/US2015/011837, filed Jan. 16, 2015, which was published in English under PCT Article 21(2), and claims the benefit of U.S. Provisional Application No. 61/928,909, filed Jan. 17, 2014, which is incorporated by reference herein in its entirety.

ACKNOWLEDGMENT OF GOVERNMENT SUPPORT

This invention was made with government support under AI081218 awarded by the National Institutes of Health. The government has certain rights in the invention.

FIELD

The invention concerns particle formulations of all-trans retinoic acid and transforming growth factor beta for the treatment of autoimmune diseases, such as type I diabetes mellitus. Methods of making and using the particle formulations are also disclosed.

BACKGROUND

Autoimmune diseases may be caused by potentially harmful white blood cells called T cells. These T cells can sometimes destroy the body's own tissues and cells. Inactivation of these self-reactive T cells can reverse disease progression. Such inactivation can be accomplished by programming the behaviors of another type of white blood cells called dendritic cells (DCs).

Diabetes mellitus results from the failure of cells to transport endogenous glucose across their membranes either because of an endogenous deficiency of insulin or an insulin receptor defect. Diabetes type 1 is caused by the destruction of β cells, which results in insufficient levels of endogenous insulin. Diabetes type 2 may initiate as a defect in either the insulin receptor itself or in the number of insulin receptors present or in the balance between insulin and glucagon signals, although it is ultimately caused due to a loss of functional β cells. Current treatment of individuals with clinical manifestation of diabetes attempts to emulate the role of the pancreatic β cells in a non-diabetic individual. Individuals with normal β cell function exhibit precise regulation of insulin secretion in response to serum glucose levels. This regulation is due to a feedback mechanism that resides in the β cells that ordinarily prevents surges of blood sugar outside of the normal limits. Unless blood sugar is controlled properly, dangerous or even fatal levels can result. Hence, treatment of a diabetic individual involves monitoring of blood glucose levels and the use of injected bovine, porcine, or cloned human insulin as required. Despite such intervention, there is often a gradual decline in the health of diabetics. Diabetes afflicts millions of people in the United States alone, and there is a clear need to provide additional treatments for this disease.

SUMMARY

Particle formulations that include polymeric particles containing a small molecule drug and a high molecular weight therapeutic protein are disclosed herein. Methods of making and using these particle formulations also are disclosed.

In some embodiments, the particle formulation includes a particle comprising all-trans retinoic acid (ATRA) encapsulated within a polymeric matrix, and at least one molecule of transforming growth factor beta (TGFβ) adsorbed on a surface of the particle. In some examples, the polymeric matrix comprises poly-(d, l-lactic-co-glycolic) acid (PLGA). In additional embodiments, the particle can have a diameter ranging from 500 nm to 2000 nm.

In certain embodiments, the particle further includes a metal-chelating compound. The metal may be nickel, zinc, copper, iron, or cobalt. In some embodiments, the metal chelating compound is a nickel-chelating lipid, e.g., 1,2-dioleoyl-sn-glycero-3-[(N-(5-amino-1-carboxypentyl)iminodiacetic acid)succinyl] (nickel salt). Histidine-tagged TGFβ is adsorbed to the particle surface via metal coordination with the histidine. Alternatively, histidine-tagged streptavidin is adsorbed to the particle surface via metal coordination, and biotinylated TGFβ binds to the streptavidin.

In additional embodiments, the disclosed particle formulations are made by preparing a solution comprising the ATRA, a polymer, and a solvent, emulsifying the solution with water and optionally an emulsifying agent, evaporating the solvent to produce a polymeric particle including encapsulated ATRA, and adsorbing TGFβ onto the polymeric particle. The solution may further include a metal-chelating compound, such as a nickel chelating lipid. In one embodiment, the TGFβ is histidine-tagged TGFβ. In another embodiment, the TGFβ is biotinylated, and the method further includes combining the polymeric particle with histidine-tagged streptavidin (H6-SA) to produce a H6-SA/polymeric particle, and subsequently combining the H6-SA/polymeric particle with the biotinylated TGFβ.

In some embodiments, uses are disclosed for these particle formulations, such as for the treatment of an autoimmune disease or an inflammatory disorder. In some specific non-limiting examples, the autoimmune disease is diabetes.

The foregoing and other objects and features of the disclosure will become more apparent from the following detailed description, which proceeds with reference to the accompanying figures.

DETAILED DESCRIPTION

Particle formulations are disclosed that include polymeric particles containing a small molecule drug and a high molecular weight therapeutic protein. Methods of making and using the particle formulations also are disclosed. These particle formulations are of use to treat an autoimmune disease, such as diabetes, or an inflammatory disease.

I. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

α cells: Mature glucagon producing cells. In vivo, these cells are found in the pancreatic islets of Langerhans.

β cells: Mature insulin producing cells. In vivo, these cells are found in the pancreatic islets of Langerhans, δ cells: Mature somatostatin producing cells. In vivo, these cells are found in the pancreatic islets of Langerhans.

PP cells: Mature pancreatic polypeptide (PP) producing cells. In vivo, these cells are found in the pancreatic islets of Langerhans.

ε cells: Mature ghrelin producing cells. In vivo, these cells are found in the pancreatic islets of Langerhans.

Administration: To provide or give a subject an agent by any effective route. Exemplary routes of administration include, but are not limited to, oral, injection (such as subcutaneous, intramuscular, intradermal, intraperitoneal, intravenous, and intratumoral), sublingual, rectal, transdermal, intranasal, vaginal and inhalation routes.

Agent: Any polypeptide, compound, small molecule, organic compound, salt, polynucleotide, or other molecule of interest, such as polymeric particles containing a small molecule drug and a high molecular weight therapeutic protein. Agent can include a therapeutic agent, a diagnostic agent or a pharmaceutical agent. A therapeutic agent is a substance that demonstrates some therapeutic effect by restoring or maintaining health, such as by alleviating the symptoms associated with a disease or physiological disorder, or delaying (including preventing) the disease.

Animal: Living multi-cellular vertebrate organisms, a category that includes, for example, mammals and birds. The term mammal includes both human and non-human mammals. Similarly, the term "subject" includes both human and veterinary subjects.

Anti-diabetic lifestyle modifications: Changes to lifestyle, habits, and practices intended to alleviate the symptoms of diabetes or pre-diabetes. Obesity and sedentary lifestyle may both independently increase the risk of a subject developing type II diabetes, so anti-diabetic lifestyle modifications include those changes that will lead to a reduction in a subject's body mass index (BMI), increase physical activity, or both. Specific, non-limiting examples include the lifestyle interventions described in *Diabetes Care*, 22(4):623-34 at pages 626-27, herein incorporated by reference.

Diabetes mellitus: A group of metabolic diseases in which a subject has high blood sugar, either because the pancreas does not produce enough insulin, or because cells do not respond to the insulin that is produced. Type 1 diabetes results from the body's failure to produce insulin. This form has also been called "insulin-dependent diabetes mellitus" (IDDM) or "juvenile diabetes". Type 1 diabetes mellitus is characterized by loss of the insulin-producing βcells, leading to insulin deficiency. This type can be further classified as immune-mediated or idiopathic. Type 2 diabetes results from insulin resistance, a condition in which cells fail to use insulin properly, sometimes combined with an absolute insulin deficiency. This form is also called "non insulin-dependent diabetes mellitus" (NIDDM) or "adult-onset diabetes." The defective responsiveness of body tissues to insulin is believed to involve the insulin receptor. Diabetes mellitus is characterized by recurrent or persistent hyperglycemia, and is diagnosed by demonstrating any one of:

a. Fasting plasma glucose level≥7.0 mmol/l (126 mg/dl);
b. Plasma glucose≥11.1 mmol/l (200 mg/dL) two hours after a 75 g oral glucose load as in a glucose tolerance test;
c. Symptoms of hyperglycemia and casual plasma glucose≥11.1 mmol/l (200 mg/dl);
d. Glycated hemoglobin (Hb A1C)≥6.5%.

Effective amount or Therapeutically effective amount: The amount of agent, such as polymeric particles containing a small molecule drug and a high molecular weight therapeutic protein, that is an amount sufficient to prevent, treat (including prophylaxis), reduce and/or ameliorate the symptoms and/or underlying causes of any of a disorder or disease. In one embodiment, an "effective amount" is sufficient to reduce or eliminate a symptom of a disease, such as a diabetes. In another embodiment, an effective amount is an amount sufficient to overcome the disease itself.

Endocrine: Tissue which secretes regulatory hormones directly into the bloodstream without the need for an associated duct system.

Exocrine tissue: Secretory tissue which distributes its products, such as enzymes, via an associated duct network. The exocrine pancreas is the part of the pancreas that secretes enzymes required for digestion. The exocrine cells of the pancreas include the centroacinar cells and basophilic cells, which produce secretin and cholecystokinin.

Fasting plasma glucose (FPG): A diagnostic test for diabetes or pre-diabetes. The blood glucose concentration or level of a subject is analyzed in a blood sample obtained from a subject after the subject has fasted overnight or undergone a fast of at least 8 hours. A diabetic subject will often show a heightened blood glucose level, compared to a non-diabetic subject. Generally, a fasting plasma glucose test (FPG) is used to determine if a subject has impaired fasting glucose. An FPG of greater than 100 mg/dl and less than 126 mg/dl indicates that a subject has pre-diabetes. A FPG greater than or equal to 126 mg/dl indicates that a subject has frank diabetes, and an FPG of equal to or less than 100 mg/dl indices that subject is normal (healthy) and does not have pre-diabetes or diabetes. For example, the subject is not known to have diabetes type 2, and/or does not satisfy diagnostic criteria for diabetes type 2 and pre-diabetes.

Inhibiting or treating a disease: Inhibiting the full development of a disease, disorder or condition, for example, in a subject who is at risk for a disease such as diabetes. "Treatment" refers to a therapeutic intervention that ameliorates a sign or symptom of a disease or pathological condition after it has begun to develop. As used herein, the term "ameliorating," with reference to a disease, pathological condition or symptom, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease.

Insulin: A hormone that has extensive effects on metabolism and other body functions, such as vascular compliance. Insulin causes cells in the liver, muscle, and fat tissue to take up glucose from the blood, storing it as glycogen in the liver and muscle, and stopping use of fat as an energy source. In mammals, insulin is synthesized in the pancreas within the beta cells (β-cells) of the islets of Langerhans.

When insulin is absent (or low), glucose is not taken up by body cells, and the body begins to use fat as an energy source, for example, by transfer of lipids from adipose tissue to the liver for mobilization as an energy source. As its level is a central metabolic control mechanism, its status is also used as a control signal to other body systems (such as amino acid uptake by body cells). It has several other anabolic effects throughout the body. When control of insulin levels fails, diabetes mellitus may result.

The human insulin gene is located on chromosome Up15.5, between the tyrosine hydroxylase (TH) and insulin-like growth factor-2 (IGF2) genes as reviewed in Sander M. and German M. S. 1997 *J Mol Med* 75:327-340. The published sequence of the human preproinsulin gene is available at GenBank Accession No. V00565. The human insulin gene contains three exons and two introns. The final spliced mRNA transcript is 446 bp in length and codes for the preproinsulin peptide. The structure of the insulin gene has been remarkably well conserved throughout evolution. Most animals have a single copy of the insulin gene, with the exception of rat and mouse which carry a duplication of the gene.

Evolutionary conservation of the insulin gene extends to the promoter sequence, which is important for insulin expression, as it determines the transcription start site for RNA polymerase and regulates the rate of transcription initiation. The promoter consists of all the 5' flanking DNA necessary for appropriate initiation of transcription. The exact 5' end of the promoter is not well defined, but it is known that sequences at least 4 kb upstream contribute to the regulation of transcription.

Islets of Langerhans: Small discrete clusters of pancreatic endocrine tissue. In vivo, in an adult mammal, the islets of Langerhans are found in the pancreas as discrete clusters (islands) of pancreatic endocrine tissue surrounded by the pancreatic exocrine (or acinar) tissue. In vivo, the islets of Langerhans consist of the α cells, β cells, δ cells, PP cells, and ε cells. Histologically, in rodents, the islets of Langerhans consist of a central core of β cells surrounded by an outer layer of α cells, δ cells, and PP cells. The structure of human islets of Langerhans is different and distinct from rodents. The islets of Langerhans are sometimes referred to herein as "islets."

Isolated: An "isolated" biological component (such as a nucleic acid, peptide or protein) has been substantially separated, produced apart from, or purified away from other biological components in the cell of the organism in which the component naturally occurs, i.e., other chromosomal and extrachromosomal DNA and RNA, and proteins. Nucleic acids, peptides and proteins which have been "isolated" thus include nucleic acids and proteins purified by standard purification methods. The term also embraces nucleic acids, peptides and proteins prepared by recombinant expression in a host cell as well as chemically synthesized nucleic acids. An isolated cell type has been substantially separated from other cell types, such as a different cell type that occurs in an organ. A purified cell or component can be at least 90%, at least 95%, at least 96%, at least 97%, at least 98%, or at least 99% pure.

Label: A detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes.

Mammal: This term includes both human and non-human mammals. Similarly, the term "subject" includes both human and veterinary subjects.

Oral glucose tolerance test (OGTT): A diagnostic test for diabetes. After fasting overnight, a subject is provided a concentrated sugar solution to drink, usually containing 50 to 100 grams of glucose. The subject's blood is sampled periodically over the next few to several hours to test blood glucose levels over time. In a non-diabetic subject, blood glucose concentration shows a slight upward shift and returns to normal within 2-3 hours. In a diabetic subject, blood glucose concentration is generally higher than normal after fasting, rises more after the subject drinks the glucose solution, and may take several hours to return to normal. An OGTT of greater than or equal to 140 mg/dl and less than 200 mg/dl indicates that a subject has pre-diabetes. An OGTT of greater than or equal to 200 mg/dl indicates that a subject has frank diabetes, and an OGTT of less than 140 mg/dl indicates that a subject is normal (healthy) and does not have pre-diabetes or diabetes.

Overweight: An individual who weighs more than their ideal body weight. An overweight individual can be obese, but is not necessarily obese. In one embodiment, an overweight human individual is any individual who desires to decrease their weight. In another embodiment, an overweight human individual is an individual with a BMI of 25.0 kg/m$^2$ to 29.9 kg/m$^2$.

Pancreatic endocrine cell: An endocrine cell of pancreatic origin that produces one or more pancreatic hormone, such as insulin, glucagon, somatostatin, or pancreatic polypeptide. Subsets of pancreatic endocrine cells include the α (glucagon producing), β (insulin producing), δ (somatostatin producing) or PP (pancreatic polypeptide producing) cells. Additional subsets produce more than one pancreatic hormone, such as, but not limited to, a cell that produces both insulin and glucagon, or a cell that produces insulin, glucagon, and somatostatin, or a cell that produces insulin and somatostatin.

Pharmaceutically acceptable carriers: The pharmaceutically acceptable carriers useful in this invention are conventional. *Remington's Pharmaceutical Sciences*, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pre-diabetes: A state in which some, but not all, of the criteria for diabetes are met. For example, a subject can have impaired fasting glycemia or impaired fasting glucose (IFG). Subjects with fasting glucose levels from 110 to 125 mg/dl (6.1 to 6.9 mmol/l) are considered to have impaired fasting glucose. Subjects with plasma glucose at or above 140 mg/dL (7.8 mmol/L), but not over 200 mg/dL (11.1 mmol/L), two hours after a 75 g oral glucose load are considered to have impaired glucose tolerance.

Predisposition for diabetes: A subject that is at high risk for developing diabetes. A number of risk factors are known to those of skill in the art and include: genetic factors (e.g., carrying alleles that result in a higher occurrence of diabetes than in the average population or having parents or siblings with diabetes); overweight (e.g., body mass index (BMI) greater or equal to 25 kg/m$^2$); habitual physical inactivity, race/ethnicity (e.g., African-American, Hispanic-American, Native Americans, Asian-Americans, Pacific Islanders); previously identified impaired fasting glucose or impaired glucose tolerance, hypertension (e.g., greater or equal to 140/90 mmHg in adults); HDL cholesterol less than or equal to 35 mg/dl; triglyceride levels greater or equal to 250 mg/dl; metabolic syndrome a history of gestational diabetes or delivery of a baby over nine pounds; and/or polycystic ovary syndrome. See, e.g., "Report of the Expert Committee on the Diagnosis and Classification of Diabetes Mellitus" and "Screening for Diabetes" Diabetes Care 25(1): S5-S24 (2002).

Polypeptide: A polymer in which the monomers are amino acid residues that are joined together through amide bonds. When the amino acids are alpha-amino acids, either the L-optical isomer or the D-optical isomer can be used, the L-isomers being preferred. The terms "polypeptide" or "protein" as used herein is intended to encompass any amino acid sequence and include modified sequences such as glycoproteins. The term "polypeptide" is specifically intended to cover naturally occurring proteins, as well as those that are recombinantly or synthetically produced.

The term "polypeptide fragment" refers to a portion of a polypeptide which exhibits at least one useful epitope. The term "functional fragments of a polypeptide" refers to all fragments of a polypeptide that retain an activity of the polypeptide. Biologically functional fragments, for example, can vary in size from a polypeptide fragment as small as an epitope capable of binding an antibody molecule to a large polypeptide capable of participating in the characteristic induction or programming of phenotypic changes within a cell. An "epitope" is a region of a polypeptide capable of binding an immunoglobulin generated in response to contact with an antigen. Thus, smaller peptides containing the biological activity of insulin, or conservative variants of the insulin, are thus included as being of use.

The term "soluble" refers to a form of a polypeptide that is not inserted into a cell membrane.

The term "substantially purified polypeptide" as used herein refers to a polypeptide which is substantially free of other proteins, lipids, carbohydrates or other materials with which it is naturally associated. In one embodiment, the polypeptide is at least 50%, for example at least 80% free of other proteins, lipids, carbohydrates or other materials with which it is naturally associated. In another embodiment, the polypeptide is at least 90% free of other proteins, lipids, carbohydrates or other materials with which it is naturally associated. In yet another embodiment, the polypeptide is at least 95% free of other proteins, lipids, carbohydrates or other materials with which it is naturally associated.

Conservative substitutions replace one amino acid with another amino acid that is similar in size, hydrophobicity, etc. Variations in the cDNA sequence that result in amino acid changes, whether conservative or not, should be minimized in order to preserve the functional and immunologic identity of the encoded protein. The immunologic identity of the protein may be assessed by determining if it is recognized by an antibody; a variant that is recognized by such an antibody is immunologically conserved. Any cDNA sequence variant will preferably introduce no more than twenty, and preferably fewer than ten amino acid substitutions into the encoded polypeptide. Variant amino acid sequences may, for example, be 80, 90 or even 95% or 98% identical to the native amino acid sequence.

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are.

Methods of alignment of sequences for comparison are well known in the art. Various programs and alignment algorithms are described in: Smith and Waterman (*Adv. Appl. Math.* 2: 482, 1981); Needleman and Wunsch (*J. Mol. Biol.* 48: 443, 1970); Pearson and Lipman (*PNAS. USA* 85: 2444, 1988); Higgins and Sharp (*Gene,* 73: 237-244, 1988); Higgins and Sharp (*CABIOS* 5: 151-153, 1989); Corpet et al. (*Nuc. Acids Res.* 16: 10881-10890, 1988); Huang et al. (*Comp. Appls Biosci.* 8: 155-165, 1992); and Pearson et al. (*Meth. Mol. Biol.* 24: 307-31, 1994). Altschul et al. (*Nature Genet.*, 6: 119-129, 1994) presents a detailed consideration of sequence alignment methods and homology calculations.

The alignment tools ALIGN (Myers and Miller, *CABIOS* 4:11-17, 1989) or LFASTA (Pearson and Lipman, 1988) may be used to perform sequence comparisons (Internet Program© 1996, W. R. Pearson and the University of Virginia, "fasta20u63" version 2.0u63, release date December 1996). ALIGN compares entire sequences against one another, while LFASTA compares regions of local similarity. These alignment tools and their respective tutorials are available on the Internet at the NCSA Website. Alternatively, for comparisons of amino acid sequences of greater than about 30 amino acids, the "Blast 2 sequences" function can be employed using the default BLOSUM62 matrix set to default parameters, (gap existence cost of 11, and a per residue gap cost of 1). When aligning short peptides (fewer than around 30 amino acids), the alignment should be performed using the "Blast 2 sequences" function, employing the PAM30 matrix set to default parameters (open gap 9, extension gap 1 penalties). The BLAST sequence comparison system is available, for instance, from the NCBI web site; see also Altschul et al., *J. Mol. Biol.* 215:403-410, 1990; Gish. & States, *Nature Genet.* 3:266-272, 1993; Madden et al. *Meth. Enzymol.* 266:131-141, 1996; Altschul et al.,

*Nucleic Acids Res.* 25:3389-3402, 1997; and Zhang & Madden, *Genome Res.* 7:649-656, 1997.

Orthologs (equivalent to proteins of other species) of proteins are in some instances characterized by possession of greater than 75% sequence identity counted over the full-length alignment with the amino acid sequence of specific protein using ALIGN set to default parameters. Proteins with even greater similarity to a reference sequence will show increasing percentage identities when assessed by this method, such as at least 80%, at least 85%, at least 90%, at least 92%, at least 95%, or at least 98% sequence identity. In addition, sequence identity can be compared over the full length of one or both binding domains of the disclosed fusion proteins.

When significantly less than the entire sequence is being compared for sequence identity, homologous sequences will typically possess at least 80% sequence identity over short windows of 10-20, and may possess sequence identities of at least 85%, at least 90%, at least 95%, or at least 99% depending on their similarity to the reference sequence. Sequence identity over such short windows can be determined using LFASTA; methods are described at the NCSA Website. One of skill in the art will appreciate that these sequence identity ranges are provided for guidance only; it is entirely possible that strongly significant homologs could be obtained that fall outside of the ranges provided. Similar homology concepts apply for nucleic acids as are described for protein.

An alternative indication that two nucleic acid molecules are closely related is that the two molecules hybridize to each other under stringent conditions. Stringent conditions are sequence-dependent and are different under different environmental parameters. Generally, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Conditions for nucleic acid hybridization and calculation of stringencies can be found in Sambrook et al. (In *Molecular Cloning: A Laboratory Manual,* Cold Spring Harbor, N.Y., 1989) and Tijssen (*Laboratory Techniques in Biochemistry and Molecular Biology* Part 1, Ch. 2, Elsevier, N.Y., 1993).

Nucleic acid sequences that do not show a high degree of identity may nevertheless encode similar amino acid sequences, due to the degeneracy of the genetic code. It is understood that changes in nucleic acid sequence can be made using this degeneracy to produce multiple nucleic acid sequences that each encode substantially the same protein.

Subject: Any mammal, such as humans, non-human primates, pigs, sheep, cows, rodents, cats, dogs, and the like which is to be the recipient of the particular treatment. In two non-limiting examples, a subject is a human subject or a murine subject.

Transforming Growth Factor Beta (TGF-β): A growth factor and immunomodulatory cytokine that is secreted from cells and acts through specific binding interactions with a collection of different cell-surface localized receptors. TGF-β1 is the prototype for a large family of secreted polypeptides that includes the mammalian TGF-β isoforms (TGF-β1, TGF-β2, and TGF-β3), bone morphogenesis proteins (BMPs), activins, and Müllerian inhibitory substance (MIS). In general, TGF-β family proteins are homodimers, wherein each functional protein complex includes two identical, associated monomer subunits. The crystal structure of the TGF-β1 homodimer is known (Hinck et al., *Biochem.,* 35:8517-8534, 1996; Qian et al., *J. Biol. Chem.,* 271:30656-30662, 1996). TGF-β is a very compact protein, having four intramolecular disulfide bridges within each subunit, as well as one intermolecular disulfide bridge.

Each monomer of the protein is synthesized as a large (~55 kDa) precursor molecule with a long (about 278 residue) N-terminal pro-region and a much shorter (112 residue, 12.5 kDa) C-terminal active domain (the mature region). During the maturation process, two precursor molecules associate with each other; the pro-region is important for proper folding of and proper association between the two active domain monomers. The pro-region of each monomer is proteolytically cleaved from the associated active domain; in most instances however, the pro-region remains associated with the mature TGF-β fragment. The severed pro-region is referred to as the "latency-associated peptide" (LAP), which is responsible for blocking the correctly folded TGF-β homodimer so that it does not interact with its receptor. Members of the TGF-β family initiate their cellular action by binding to three high affinity receptors designated as types I, II, and III (endoglin is another TGF-β receptor that is abundant on endothelial cells).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

II. Particle Formulations Method of Making

Figure 1:
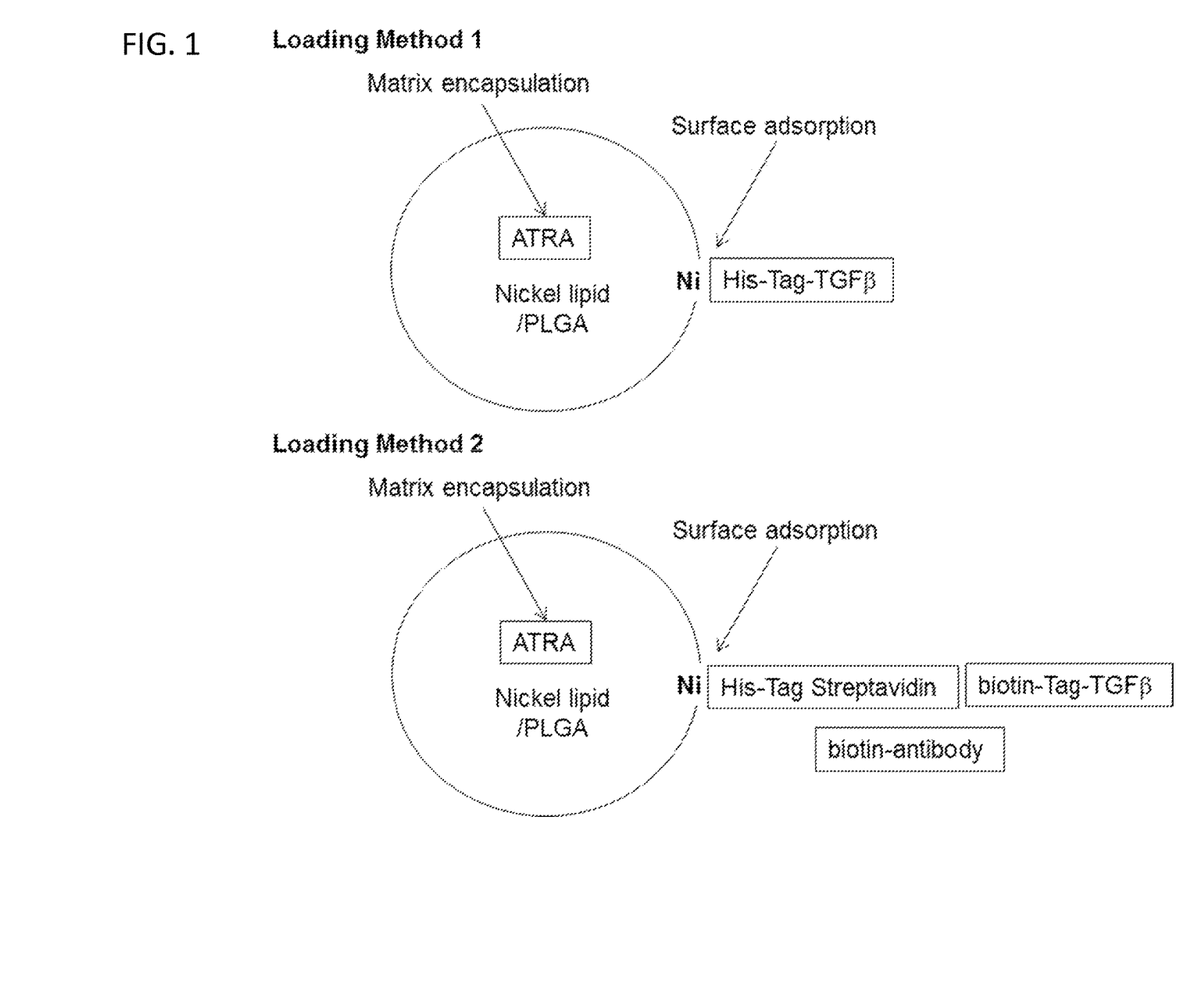
FIG. 1 is a diagram illustrating two exemplary embodiments of particle formulations comprising polymeric particles containing all-trans retinoic acid (ATRA) and transforming growth factor beta (TGFβ).

Embodiments of particle formulations comprising polymeric particles containing a small molecule drug and a high molecular weight therapeutic protein are disclosed. In some embodiments, the particle formulations comprise all-trans retinoic acid (ATRA) and transforming growth factor beta (TGFβ). In such embodiments, TGFβ is adsorbed on the particle surface and ATRA is encapsulated within the particle (FIG. 1). The disclosed particles may be nanoparticles or microparticles. ATRA has the structure:

The disclosed particle formulations are prepared by first encapsulating the small molecule drug within a polymeric matrix to form polymeric particles containing the drug. Suitable polymeric matrices include, but are not limited to, poly-(d, 1-lactic-co-glycolic) acid (PLGA), polylactic acid (PLA), poly(ε-caprolactone), polyketals (e.g., poly(cyclohexane-1,4-diylacetone dimethylene ketal (PCADK)), poly (phosphoesters), dextran and dextran derivatives, chitosan, poly(ortho esters), and polyphosphazenes.

In some embodiments, the small molecule drug is ATRA and encapsulation is accomplished by an emulsification process utilizing PLGA as a drug dispersal matrix. Such process results in dispersal of ATRA within the biodegradable polymeric matrix, thereby circumventing the drug's poor water solubility and protecting the drug from chemical degradation. The PLGA may have a ratio of lactic acid and glycolic acid ranging from 1:20 to 20:1, such as from 1:10 to 10:1, 1:5 to 5:1, or 1:3 to 3:1. In some embodiments, the PLGA comprises from 25-95 mol % lactic acid, such as from 45-95 mol %. The PLGA may have an average molecular weight (weight average molecular weight/number average molecular weight, e.g., as measured by gel permeation chromatography) from 3,000 to 40,000 kDa, such as from 5,000 to 25,000 kDa, 10,000 to 25,000 kDa, or 15,000 to 25,000 kDa.

On the other hand, therapeutic proteins such as TGFβ are susceptible to damage (denaturation) during the same fabrication process. This problem is circumvented by loading TGFβ after particle formation. In some embodiments, the particle further comprises a nickel-chelating lipid, and the TGFβ is adsorbed to the particle surface through biochemical means, such as metal coordination. For example, the TGFβ may be tagged with histidine (His-Tag), which coordinates with certain metals, including nickel ($Ni^{2+}$) (FIG. 1, upper diagram), zinc ($Zn^{2+}$), copper ($Cu^{2+}$), iron ($Fe^{3+}$), and cobalt ($Co^{2+}$). Histidine coordinates with varying affinities to the metal ions. In certain embodiments, TGFβ is adsorbed to the particle surface through nickel coordination.

Metals may be introduced onto the particle's surface by including a metal-chelating compound in the particle. Suitable metal-chelating compounds include, but are not limited to, iminodiacetic acid (IDA, e.g., Ni-IDA), aminopolycarboxylates (such as nitrilotriacetic acid (NTA, e.g., Ni-NTA)), and carboxymethyl aspartate (CMA, e.g., Co-CMA) moieties, and metal-chelating lipids comprising such moieties, such as 1,2-dioleoyl-sn-glycero-3-[(N-(5-amino-1-carboxypentyl)iminodiacetic acid)succinyl] (ammonium salt) (DOGS-NTA, e.g., DOGS-NTA-Ni), 1-paomitoyl-2-[8-[(E,E)-2', 4'-hexadienolyloxyloctanoyl]-sn-glycero-3-N-[11-[N',N'-bis[carboxymethyl]imino-3,6,9-trioxaundecanoyl] phosphatidylethanolamine (which chelates Cu through an IDA moiety), and lipid distearyl imino-diacetate (DSIDA, e.g., Cu-DSIDA). In some embodiments, the metal-chelating compound is Ni-IDA, Ni-NTA, Co-CMA, or DOGS-NTA-Ni. In certain examples, the metal-chelating compound is DOGS-NTA-Ni. In some embodiments, the biodegradable polymer and metal-chelating compound are present in a molar ratio from 20:1 to 2:1, such as from 15:1 to 3:1 or from 10:1 to 5:1.

In some embodiments, the TGFβ is linked to several consecutive histidine residues. For example, the TGFβ can be conjugated to several consecutive histidine residues, such as 2, 3, 4, 5, 6, 7, 8, 9, 10 or more histidine residues. The histidine residues can be, for example, covalently linked to the N-terminus of the TGFβ polypeptide or covalently linked to the C-terminus of the TGFβ polypeptide.

Alternatively, histidine-tagged streptavidin may be adsorbed to the particle surface, and biotinylated TGFβ is utilized, which binds to the streptavidin (FIG. 1, lower diagram). These specific and high affinity interactions allow controlling the dose of TGFβ loaded. For example, the streptavidin can be conjugated to several consecutive histidine residues, such as 2, 3, 4, 5, 6, 7, 8, 9, 10 or more histidine residues. The histidine residues can be, for example, covalently linked to the N-terminus of the streptavidin or covalently linked to the C-terminus of the streptavidin.

An exemplary amino acid sequence of TGFβ is provided as GENBANK® Accession No. TGFB1_HUMAN, Dec. 11, 2013, incorporated herein by reference. Any TGFβ can be used in the methods disclosed herein. The amino acid sequence of the homo sapiens transforming growth factor 1 precursor is provided in GENBANK® Accession No. NP_000651.3, May 26, 2014, incorporated by reference herein. The amino acid sequence of the mouse TGFβ precursor is provided in GENBANK® Accession No. NP_035707.1, May 25, 2014, incorporated by reference herein.

Conservative variants and fragments that retain the function of TGFβ are also of use. For example, the TGFβ polypeptide can include at most 1, 2, 3, 4, 5, 6, 7, 8, 9, or 10 conservative amino acid substitutions, such that the biological function of the TFG-β is not altered by the substitutions. Generally, "conservative" substitutions are likely to have minimal impact on the activity of the resultant protein, especially when made outside of the binding site of each domain. The table below shows amino acids that may be substituted for an original or native amino acid in a protein, and which are regarded as conservative substitutions.

| Original Residue | Conservative Substitutions |
| --- | --- |
| Ala | ser |
| Arg | lys |
| Asn | gln; his |
| Asp | glu |
| Cys | ser |
| Gln | asn |
| Glu | asp |
| Gly | pro |
| His | asn; gln |
| Ile | leu; val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

In additional embodiments, the TGFβ polypeptide can be, for example, at least 90%, 91%, 92%, 93%, 94%, 95%, 96%, 97%, 98% or 99% identical to a wild-type TGFβ polypeptide. One of skill in the art can readily identify additional TGFβ polypeptides of use.

Particles comprising ATRA may be prepared using a solvent evaporation method. A solvent, or mixture of solvents, capable of dissolving ATRA, the desired biodegradable polymer, and the metal-chelating compound is used. Suitable solvents include, but are not limited to, chloroform, dichloromethane (DMC), 1,2-dichloroethane, 1,1-dichloroethane, 1,2-dichloropropane, monofluoromethane, difluoromethane, 2-methyltetrahydrofuran (MeTHF), ethyl acetate, methanol, ethanol, acetone, dimethyl sulfoxide, and combinations thereof. ATRA, the biodegradable polymer, and the metal-chelating compound may be combined in a single solution or prepared as separate solutions.

The solutions are emulsified in a large volume of water, and the organic solvent is subsequently evaporated to produce solid particles comprising ATRA, the biodegradable polymer, and the metal-chelating compound. The water may include an emulsifying agent to lower the surface tension and reduce or prevent aggregation of molecules and nanoparticles at the hydrophilic/hydrophobic interface. Suitable emulsifying agent include nonionic and/or polymeric surfactants, such as polyvinyl alcohol (PVA), poly(ethylene glycol) (PEG), glycerin, propylene glycol, polysorbates (e.g., polyoxyethylene (20) sorbitan monooleate (TWEEN® 80, polysorbate 80), polyoxyethylene (20) sorbitan monolaurate (TWEEN® 20, polysorbate 20), polyoxyethylene (20) sorbitan monostearate (polysorbate 60), polyoxyethylene (20) sorbitan monopalmitate (polysorbate 40)), polyoxyethylene (20) sorbitan trioleate, polyoxyethylene (8) octylphenyl ether, polyoxyethylene (20) cholesterol ester, polyoxyethylene (30) cholesterol ester, polyoxyethylene (20) cetyl ether, (BRIJ® 58), polyoxytheylene-hardened castor oil, and combinations thereof. In certain embodiments, the solvent is DCM and the surfactant is PVA.

Evaporation of the solvent from the emulsion produces solid polymer-ATRA particles with metal atoms embedded on the surface. The particles can be washed and recovered by convention centrifugation. The particles are referred to as "polymer-metal/ATRA," such as "PLGA-Ni/ATRA." Particles are lyophilized into dried powder under reduced pressure. Particle sizes are adjusted by varying the concentrations of emulsifying agent (e.g., polyvinyl alcohol) and the starting drug amount. In one example, the particles had a substantially spherical morphology, and a diameter ranging from 500 nm to 2000 nm, such as from 590 nm to 1800 nm.

In some embodiments, solutions of ATRA, PLGA, and DOGS-NTA-Ni dissolved in DCM are emulsified in a larger volume of water containing PVA (Kovacs et al., 2009). Evaporation of DCM results in solid PLGA-Ni/ATRA particles that can be washed and recovered by conventional centrifugation.

Embodiments of the disclosed polymer-metal/ATRA particles gradually release ATRA under physiologic conditions, e.g., at 37° C. in phosphate buffered saline. In some embodiments, ATRA is released continuously for at least about 5, 6, 7, 8, 9, 10, 11, 12, 13, 14, 15, 16, 17, 18, 19 or 20 days from polymer-metal/ATRA. In additional embodiments, ATRA is released continuously for at least about 5, 6, 7, 8, 9, 10, 11, 12, 13, 14, 15, 16, 17, 18, 19 or 20 days from PLGA-Ni/ATRA particles. In one non-limiting example, ATRA is released continuously for at least 10 days from PLGA-Ni/ATRA particles. For example, up to 20% of the ATRA may be released over a period of 10 days. In one example, approximately 4% of the ATRA was released after one day, and approximately 17% was released after 10 days. The rate of release can be adjusted by changing the ratio of lactic and glycolic acids in the polymer. In some embodiments, the ratio of lactic acid and glycolic acid ranges from 1:3 to 3:1, such as 1:3, 1:2, 1:1, 2:1, or 3:1. In certain examples, the ratio of lactic and glycolic acids was 1:1.

TFGβ is loaded onto the polymer-metal/ATRA particles. In one exemplary method, His-tagged TGFβ is adsorbed onto PLGA-Ni via nickel coordination with histidines (FIG. 1, upper diagram). The protein is incubated with specific densities of the particles suspended in buffered saline at ambient temperatures. In another method, biotinylated TGFβ is loaded onto the particles via His-tagged streptavidin (hereafter "H6-SA"). Tetravalent H6-SA bound on polymer-metal/ATRA particles allows surface loading of biotinylated TGFβ, which is generated using N-hydroxysuccinimidobiotin (NHS-biotin). The advantage of this design is that other biotinlyated proteins, including antibodies, can also adsorb onto the particles (FIG. 1, lower diagram).

Polymer-metal/ATRA/TGFβ particles, such as PLGA-Ni/ATRA/TGFβ particles, gradually release TGFβ under physiologic conditions, e.g., at 37° C. in phosphate buffered saline. Because histidine has different affinities for different metals, the rate of TGFβ release may be controlled, at least in part, by selection of the metal to which TGFβ or biotinylated TGFβ is coordinated via histidine. In some embodiments the metal is nickel. In additional embodiments, TGFβ is released continuously for at least, for example, about 5, 6, 7, 8, 9, 10, 11, 12, 13, 14, 15, 16, 17, 18, 19 or 20 days. In one non-limiting example, TGFβ is released continuously for at least about 10 days. In a specific, non-limiting example, the metal is nickel, and TGBβ is released continuously for at least 10 days.

In some embodiments, the rate of release averages from about 1 ng/mL to about 10 ng/mL, such as about 2 ng/mL to about 10 ng/mL, such as about 5 ng/mL to about 9 ng/mL, such as about 8 ng/mL. In one non-limiting example, the average rate of release is about 8.1 to about 8.9 ng/mL, such as about 8.2 ng/mL.

In one example, PLGA-Ni/ATRA particles including biotinylated TGFβ loaded via H6-SA exhibited an average steady-state release rate of 8.2 ng/mL TGFβ per day for 10 days. This rate produces a TGFβ concentration well above the physiologically-active concentration of the cytokine ($ED_{50}$ of 0.04-0.2 ng/mL; Tsang et al., *Cytokine* 7:389-97 (1995)).

Embodiments of the disclosed polymer-metal/ATRA/TGFβ particles advantageously provide coadministration of ATRA and TGFβ with gradual release of ATRA and/or TGFβ. In some embodiments, gradual, sustained release of both ATRA and TGFβ is provided. The rates of release may be adjusted by varying the biodegradable polymer, the ratio of monomers within a biodegradable polymer (e.g., PLGA), and/or by selection of the metal to which TGFβ or biotinylated TGFβ is coordinated via histidine.

III. Methods of Treatment

The methods, compositions, and kits of this disclosure may comprise a treatment method to prevent, arrest, reverse, or reduce a disease. In some cases, the disease may be an autoimmune disease. Autoimmune diseases that can be treated with the disclosed particles include, but are not limited to, alopecia areata, anklosing spondylitis, antiphospholipid syndrome, asthma, arthritis, autoimmune addison's disease, autoimmune hemolytic anemia, autoimmune hepatitis, autoimmune inner ear disease, autoimmune lymphoproliferative syndrome (ALPS), autoimmune thrombocytopenic purpura (ATP), Behcet's disease, bullous pemphigoid, cardiomyopathy, celiac sprue-dermatitis, chronic fatigue syndrome immune deficiency syndrome (CFIDS), chronic inflammatory, demyelinating polyneuropathy, cicatricial pemphigoid, cold agglutinin disease, CREST syndrome, Crohn's disease, colitis, Dego's disease, dermatomyositis, discoid lupus, essential mixed cryoglobulinemia, fibromyalgia, fibromyositis, Grave's disease, Guillain-Barre, Hashimoto's thyroiditis, idiopathic pulmonary fibrosis, idiopathic thrombocytopenia purpura (ITP), IgA nephropathy, insulin dependent diabetes (Type I), juvenile arthritis, lung fibrosis, lupus, Meniere's disease, mixed connective tissue disease, multiple sclerosis, myasthenia gravis, pemphigus vulgaris, pernicious anemia, polyarteritis nodosa, polychondritis, polyglancular syndromes, polymyalgia rheumatica, polymyositis, dermatomyositis, primary agammaglobulinemia, primary biliary cirrhosis, psoriasis, Raynaud's phenomenon, Reiter's syndrome, rheumatic fever, rheumatoid arthritis, sarcoidosis, scleroderma, septic shock, Sjogren's syndrome, Stiff-Man syndrome, systemic lupus erythematosus, takayasu arteritis, temporal arteritis/Giant Cell arteritis, ulcerative colitis, uveitis, vasculitis, vitiligo, Wegener's granulomatosis, and others.

In some embodiments, the disclosed particle formulation is administered to a subject with rheumatoid arthritis, such as by intra-articular administration into an inflamed joint, or into the region where the lymph nodes draining inflamed synovia are located. In additional embodiments, the disclosed particle formulation is administered to a subject with Hashimoto's thyroiditis, such as into the neck close to the lymph nodes draining the thyroid gland.

In some embodiments the subject has type 1 diabetes. Type 1 diabetes is an autoimmune disorder where there is a progressive inflammation of the pancreas, and specifically, the endocrine insulin-producing beta cells. Before onset, the inflammation first renders the endocrine beta cells dysfunctional. In some embodiments, the disclosed particle formulation is administered to a subject with type 1 diabetes.

The disease may be an inflammatory disease. Inflammatory diseases include acne vulgaris, Alzheimer's disease, arthritis, asthma, atherosclerosis, cancer, celiac disease, chronic prostatitis, colitis, dermatitis, hepatitis, inflammatory bowel disease (IBD), interstitial cystitis, irritable bowel syndrome, multiple sclerosis, nephritis, pelvic inflammatory disease, reperfusion injury, sarcoidosis, type 1 diabetes, vasculitis and others. In some embodiments, the disclosed particle formulation is administered to a subject with inflammatory bowel disease, such as by administration into the abdomen proximal to the Peyer's Patches.

The treatment method can prevent the onset of a disease (e.g. autoimmune disease, inflammatory disease). The treatment that can arrest, reverse, or reduce the disease (e.g. autoimmune disease, inflammatory disease) after clinical onset. Without being bound by theory, a treatment method that may prevent, arrest, reverse, or reduce type 1 diabetes can include preserving viability of remaining beta cell populations, reducing inflammation, reducing blood glucose levels to pre-diabetic levels, increasing suppressive B cell populations, reducing autoreactive T cell populations, increasing tolerogenic DC populations, or combinations thereof. A treatment can prevent, arrest, reverse, or reduce an inflammatory disease (e.g. inflammatory bowel disease) and can include reducing inflammation, increasing suppressive B cell populations, reducing T cell populations, inducing RA production in DC populations, increasing tolerogenic DC populations, or combinations thereof.

In some embodiments, methods are provided for treating diabetes or pre-diabetes in a subject by administering a therapeutically effective amount of a formulation including polymeric particles containing a small molecule drug and a high molecular weight therapeutic protein to the subject. The subject can have diabetes type I. The subject can be any mammalian subject, including human subjects. The subject can be a child or an adult. The method can include selecting the subject.

The subject can be a child. A child can be less than 1, 2, 3, 4, 5, 6, 7, 8, 9, 10, 11, 12, 13, 14, 15, 16, 17 years old, or less than 18 years old. The subject can be an infant, such as a child of less than about 1 year of age. The subject can be a young child, such as between about 1 year and about 2 years of age, between about 1 year and about 3 years of age, or between about 1 year and about 5 years of age. The subject can be between about 6 years and 10 years of age, between about 6 years of age and about 12 years of age. The subject can be between about 11 years and 13 years of age. The subject can be between about 11 years and 18 years of age. The subject can be an adolescent, such as between about 13 years and 18 years of age. The subject can be an adult, such as a subject of more than 18 years of age, such as more than 20 years of age, more than 30 years of age, more than 40 years of age, or more than 50 years of age, or more than 60 years of age.

The subject can have a genetic predisposition to developing diabetes. The subject can have diabetes. The subject can also be administered insulin. In some examples, the method includes selecting a subject with diabetes, such as type I diabetes, or a subject at risk for diabetes, such as a subject with pre-diabetes.

In some examples, a subject with diabetes may be clinically diagnosed by a fasting plasma glucose (FPG) concentration of greater than or equal to 7.0 millimole per liter (mmol/L) (126 milligram per deciliter (mg/dL)), or a plasma glucose concentration of greater than or equal to 11.1 mmol/L (200 mg/dL) at about two hours after an oral glucose tolerance test (OGTT) with a 75 gram (g) load, or in a patient with classic symptoms of hyperglycemia or hyperglycemic crisis, a random plasma glucose concentration of greater than or equal to 11.1 mmol/L (200 mg/dL), or HbA1c levels of greater than or equal to 6.5%. In other examples, a subject with pre-diabetes may be diagnosed by impaired glucose tolerance (IGT). An OGTT two-hour plasma glucose of greater than or equal to 140 mg/dL and less than 200 mg/dL (7.8-11.0 mM), or a fasting plasma glucose (FPG) concentration of greater than or equal to 100 mg/dL and less than 125 mg/dL (5.6-6.9 mmol/L), or HbA1c levels of greater than or equal to 5.7% and less than 6.4% (5.7-6.4%) is considered to be IGT, and indicates that a subject has pre-diabetes. Additional information can be found in *Standards of Medical Care in Diabetes*—2010 (American Diabetes Association, *Diabetes Care* 33:S11-61, 2010, incorporated herein by reference).

In pediatric patients, a blood sugar level above 200 mg/dl can be considered high and can be characterized, in some instances, by low energy, stomachaches, and/or difficulty breathing. In pediatric patients, a blood sugar level of about 70 to about 120 mg/dl is considered normal. In pediatric patients, about 120 to about 200 mg/dl blood sugar level is considered outside the normal range, but it can be within the goal or target range for pediatric patients trying to maintain blood sugar levels. For pediatric patients aged about 12 years and older, maintaining a blood sugar level from about 70 to about 150 mg/dl can be a goal (e.g., for pediatric patients with diabetes). For pediatric patients aged about five years of age to about eleven years of age, maintaining a blood sugar level from about 70 to about 180 mg/dl can be a goal (e.g. for pediatric patients with diabetes). For pediatric patients aged about five years of age or younger, maintaining a blood sugar level from about 80 to about 200 mg/dl can be a goal (e.g., for pediatric patients with diabetes). One skilled in the art will recognize that these ranges are standard guidelines and, e.g., individual target ranges may vary based on a patient's age, body size, development, and the like.

The disclosed composition can be selected for treatment due to a partial destruction of pancreatic beta cell mass. Destruction of pancreatic beta cell mass may be inflamed tissue, expansion of fibrotic legions, cellular apoptosis, cellular necrosis, cellular loss of function (e.g. inability to produce insulin, reduced insulin production). The subject can have about: 99%, 95%, 90%, 85%, 80%, 75%, 70%, 65%, 60%, 55%, 50%, 45%, 40%, 35%, 30%, 25%, 20%, 15%, 10%, or 5% destruction of pancreatic beta cell mass. The subject can have more than about: 99%, 95%, 90%, 85%, 80%, 75%, 70%, 65%, 60%, 55%, 50%, 45%, 40%, 35%, 30%, 25%, 20%, 15%, 10%, 5% destruction of pancreatic beta cell mass. The subject can have less than about: 99%, 95%, 90%, 85%, 80%, 75%, 70%, 65%, 60%, 55%, 50%, 45%, 40%, 35%, 30%, 25%, 20%, 15%, 10%, 5% destruction of pancreatic beta cell mass.

The amount of a formulation including polymeric particles containing a small molecule drug and a high molecular weight therapeutic protein administered to the subject will be dependent on the subject being treated, the severity of the affliction, and the manner of administration, and is best left to the judgment of the prescribing clinician. Within these bounds, the formulation to be administered will contain a quantity formulation including polymeric particles containing a small molecule drug and a high molecular weight therapeutic protein in amounts effective to achieve the desired effect in the subject being treated. A therapeutically effective amount of formulation including polymeric particles containing a small molecule drug and a high molecular weight therapeutic protein can be the amount of formulation including polymeric particles containing a small molecule drug and a high molecular weight therapeutic protein that is necessary to treat diabetes or affect glucose tolerance.

A therapeutically effective amount can be administered in a single dose, twice daily, weekly, or in several doses, for example daily, or during a course of treatment. However, the therapeutically effective amount will be dependent on the subject being treated, the severity and type of the affliction, and the manner of administration of the therapeutic(s).

The compositions of this disclosure that include a formulation including polymeric particles containing a small molecule drug and a high molecular weight therapeutic protein can be administered to humans or other animals by any means, including orally, intravenously, intramuscularly, intraperitoneally, intranasally, intradermally, intrathecally, subcutaneously, via inhalation or via suppository. The formulation may be combined with a pharmaceutically acceptable carrier, such as sterile normal saline, such as phosphate buffered saline, for administration. In one non-limiting example, the composition is administered orally. In further examples, site-specific administration of the composition can be used, for example by administering a formulation including polymeric particles containing a small molecule drug and a high molecular weight therapeutic protein to pancreas tissue (for example by using a pump, or by implantation of a slow release form at the site of the pancreas).

As noted above, treatment can involve daily or multi-daily or less than daily (such as weekly or monthly etc.) doses over a period of a few days to months, or even years. In a particular non-limiting example, treatment involves a once daily dose or twice daily dose. The particular mode of administration and the dosage regimen will be selected by the attending clinician, taking into account the particulars of the case (e.g., the subject, the disease, the disease state involved, the particular treatment, and whether the treatment is prophylactic). The present disclosure also includes combinations of formulations including polymeric particles containing a small molecule drug and a high molecular weight therapeutic protein, with one or more other agents useful in the treatment of diabetes. The term "administration in combination" or "co-administration" refers to both concurrent and sequential administration of the active agents.

Anti-diabetic agents are generally categorized into six classes: biguanides; thiazolidinediones; sulfonylureas; inhibitors of carbohydrate absorption; fatty acid oxidase inhibitors and anti-lipolytic drugs; and weight-loss agents. Any of these agents can also be used in the methods disclosed herein. The anti-diabetic agents include those agents disclosed in *Diabetes Care,* 22(4):623-634, herein incorporated by reference. One class of anti-diabetic agents of use is the sulfonylureas, which are believed to increase secretion of insulin, decrease hepatic glucogenesis, and increase insulin receptor sensitivity. Another class of anti-diabetic agents of use the biguanide antihyperglycemics, which decrease hepatic glucose production and intestinal absorption, and increase peripheral glucose uptake and utilization, without inducing hyperinsulinemia.

The disclosed particle formulations can also be used in combination with insulin. The most common insulin therapy involves insulin injections before and/or after meals. Currently, injectable insulin is available, and as a general rule, is given in a subcutaneous injection. The method of administration varies depending on its time course of action. Long-acting insulin formulations such as LANATUS® (Insulin glargine; Sanofi Aventis) and LEVEMIR® (Insulin detemir; Novo Nordisk) can also be used. The disclosed particle formulations can also be used with diabetic lifestyle modifications, such as modification to diet and exercise.

In some examples, formulation including polymeric particles containing a small molecule drug and a high molecular weight therapeutic protein can be administered in combination with effective doses of anti-diabetic agents (such as biguanides, thiazolidinediones, or incretins) and/or lipid lowering compounds (such as statins or fibrates). Administration of formulation including polymeric particles containing a small molecule drug and a high molecular weight therapeutic protein, may also be in combination with lifestyle modifications, such as increased physical activity, low fat diet, low sugar diet, and smoking cessation. The formulation including polymeric particles can be used with any treatment that is of use for modulating body weight or treating diabetes.

Additional agents of use include, without limitation, anti-apoptotic substances such as the Nemo-Binding Domain and compounds that induce proliferation such as cyclin dependent kinase (CDK)-6, CDK-4 and Cyclin D1. Other active agents can be utilized, such as antidiabetic agents for example, metformin, sulphonylureas (e.g., glibenclamide, tolbutamide, glimepiride), nateglinide, repaglinide, thiazolidinediones (e.g., rosiglitazone, pioglitazone), peroxisome proliferator-activated receptor (PPAR)-gamma-agonists (such as C 1262570) and antagonists, PPAR-gamma/alpha modulators (such as KRP 297), alpha-glucosidase inhibitors (e.g., acarbose, voglibose), Dipeptidyl peptidase (DPP)-IV inhibitors (such as LAF237, MK-431), alpha2-antagonists, agents for lowering blood sugar, cholesterol-absorption inhibitors, 3-hydroxy-3-methylglutaryl-coenzyme A (HMG-CoA) reductase inhibitors (such as a statin), insulin and insulin analogues, GLP-1 and GLP-1 analogues (e.g. exendin-4) or amylin. In some embodiments the agent is an immunomodulatory factor such as anti-CD3 mAb, growth factors such as HGF, vascular endothelial growth factor (VEGF), platelet derived growth factor (PDGF), lactogens, or parathyroid hormone related protein (PTHrP)

In some examples, treating diabetes includes one or more of increasing glucose tolerance, decreasing insulin resistance (for example, decreasing plasma glucose levels, decreasing plasma insulin levels, or a combination thereof), decreasing serum triglycerides, decreasing free fatty acid levels, and decreasing HbA1c levels in the subject. In some embodiments, the disclosed methods include measuring glucose tolerance, insulin resistance, plasma glucose levels, plasma insulin levels, serum triglycerides, free fatty acids, and/or HbA1c levels in a subject.

In some examples, administration of a formulation including polymeric particles containing a small molecule drug and a high molecular weight therapeutic protein treats diabetes type I or pre-diabetes by increasing glucose tolerance, for example, by decreasing blood glucose levels (such as two-hour plasma glucose in an OGTT or FPG) in a subject. In some examples, the method includes decreasing blood glucose by at least 5% (such as at least 10%, 15%, 20%, 25%, 30%, 35%, or more) as compared with a control. In particular examples, a decrease in blood glucose level is determined relative to the starting blood glucose level of the subject (for example, prior to treatment). In other examples, decreasing blood glucose levels of a subject includes reduction of blood glucose from a starting point (for example greater than about 126 mg/dL FPG or greater than about 200 mg/dL OGTT two-hour plasma glucose) to a target level (for example, FPG of less than 126 mg/dL or OGTT two-hour plasma glucose of less than 200 mg/dL). In some examples, a target FPG may be less than 100 mg/dL. In other examples, a target OGTT two-hour plasma glucose may be less than 140 mg/dL. Methods to measure blood glucose levels in a subject (for example, in a blood sample from a subject) are routine.

In some embodiments, the disclosed methods include treating a subject with diabetes by increasing beta cell proliferation. In some examples, administration of a formulation including polymeric particles containing a small molecule drug and a high molecular weight therapeutic protein treats diabetes by increasing beta cell number in a subject, for example increasing beta cells proliferation by at least 5% (such as at least 10%, 15%, 20%, 25%, 30%, 35%, 50%, 60%, 70%, 80%, 90%, 100%, 200%, 300% or more) as compared with a control (such as the subject prior to administration of the formulation including polymeric particles containing a small molecule drug and a high molecular weight therapeutic protein). Methods of determining measuring beta cell proliferation are known in the art. The method can include measuring the number of beta cells in a sample, such as a biopsy, from the subject. The method can also include measuring incorporation of a substance incorporated into DNA, such as bromodeoxyuridine or Ki-67.

In other embodiments, the disclosed methods include comparing one or more indicator of diabetes (such as glucose tolerance, triglyceride levels, free fatty acid levels, or HbA1c levels) to a control, wherein an increase or decrease in the particular indicator relative to the control (as discussed above) indicates effective treatment of diabetes. The control can be any suitable control against which to compare the indicator of diabetes in a subject. In some embodiments, the control is a sample obtained from a healthy subject (such as a subject without diabetes). In some embodiments, the control is a historical control or standard reference value or range of values (such as a previously tested control sample, such as a group of subjects with diabetes, or group of samples from subjects that do not have diabetes). In further examples, the control is a reference value, such as a standard value obtained from a population of normal individuals that is used by those of skill in the art. Similar to a control population, the value of the sample from the subject can be compared to the mean reference value or to a range of reference values (such as the high and low values in the reference group or the 95% confidence interval). In other examples, the control is the subject (or group of subjects) treated with placebo compared to the same subject (or group of subjects) treated with the therapeutic compound in a cross-over study. In further examples, the control is the subject (or group of subjects) prior to treatment.

The disclosure is illustrated by the following non-limiting Examples.

IV. Examples

A delivery system for all-trans retinoic acid (RA) and TGFβ (TGFβ) was formulated based on poly(d,l-lactide-co-glycolide; PLGA). The methods resulted in RA dispersed within the polyester matrix, thereby circumventing the compound's poor water solubility and at the same time protecting the drug from chemical degradation. As proteins are susceptible to denaturation during the fabrication process, TGFβ was loaded after particle formation. The resultant particles have size in the submicron range. The rate of release can be adjusted by changing the ratio of lactic and glycolic acids in the polymer.

EXAMPLE 1

Preparation and Characterization of Particles

Particles comprising ATRA were prepared using a solvent evaporation method. A solution of 5 mg ATRA dissolved in 3 ml of dichloromethane (DCM) containing 90 mg of PLGA (50:50, MW: 16.5-22 kDa) and DOGS-NTA-Ni (0.6 mg, MW=1057; Avanti, Alabaster, Ala.) was prepared. This organic solution was added drop-wise into 20 ml of 1% (w/v) aqueous solution of polyvinyl alcohol (MW=22,000). This mixture was homogenized at high speed (22,000 rpm) for 5 minutes followed by slow evaporation of DCM. Evaporation of DCM resulted in solid particles. The particles were washed in water and lyophilized into dried powder under reduced pressure.

Figure 2A:
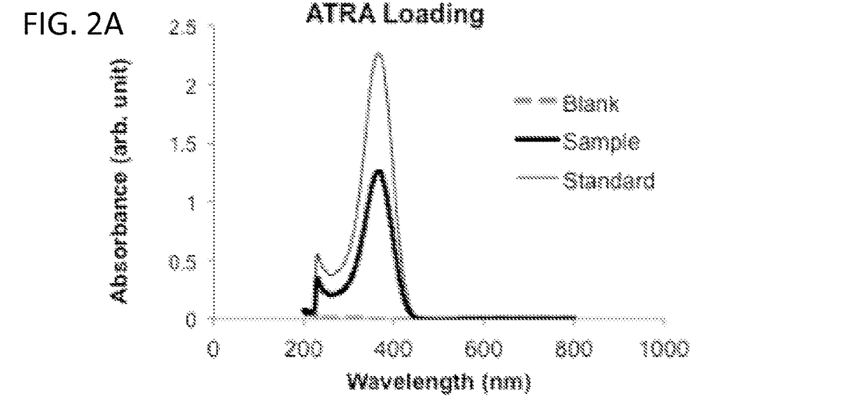
FIG. 2A is UV spectrum showing the loading efficiency of ATRA into PLGA-Ni(poly-(d, l-lactic-co-glycolic) acid/1,2-dioleoyl-sn-glycero-3-RN-[(5-amino-1-carboxypentyl)iminodiacetic acid)succinyl] (nickel salt)) particles. "Standard" refers to equivalent conc. of ATRA and PLGA dissolved; "Blank"=buffer only.

ATRA (MW=300.4) loading was determined by dissolving 10 mg of lyophilized particles in DCM, followed by extraction with DCM before UV quantification. Release of ATRA was quantified based on the UV absorbance ($\lambda=365$ nm in DCM). Peak absorbance was found at 368 nm. Preliminary studies indicated that the process resulted in satisfactory loading efficiency (59%). Using 5 mg of ATRA in the process resulted in 4.6 micrograms of the drug in each milligram of the powder (FIG. 2a). "Standard" refers to equivalent conc. of ATRA and PLGA dissolved; "Blank"=buffer only.

Figure 2B:
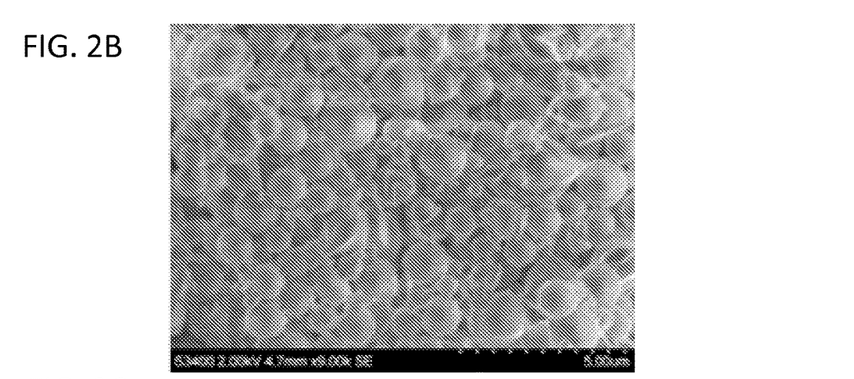
FIG. 2B is a scanning electron microscopy image (9000×) of PLGA-Ni/ATRA particles.

Scanning electron microscopic images (9000×) indicated the drug-loaded particles have near spherical shapes with diameters ranging from 590 to 1800 nm (FIG. 2b). The images were obtained using a JOEL 6500 scanning electron microscope. The particles were prepared by drying samples (10 mg/ml) by lyophilization. Sucrose was used as the cyro-protectant; diameters measured ranged from 590 nm to 1.8 µm.

Figure 2C:
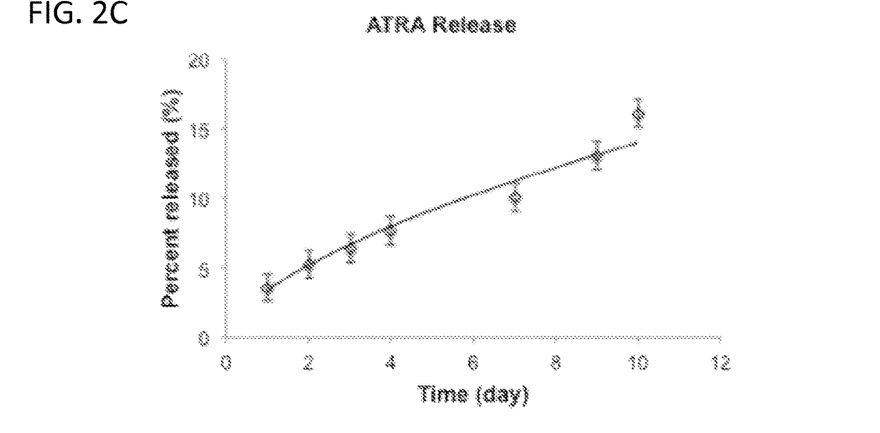
FIG. 2C is a graph illustrating the cumulative release of ATRA from PLGA-Ni/ATRA particles (10 mg/ml) at 37° C. in buffered saline.

Studies indicated that these particles released ATRA gradually at 37° C. in phosphate buffered saline (PBS) (FIG. 2c). Particles were added to PBS at a concentration of 10 mg/ml, and the cumulative release was measured over time. On day one, 2 micrograms of the drug were detected in buffer (1 ml), and a total of approximately 8 micrograms were released by day 10. The rate of release can be adjusted by changing the ratio of lactic and glycolic acids in the polymer.

Figure 3A:
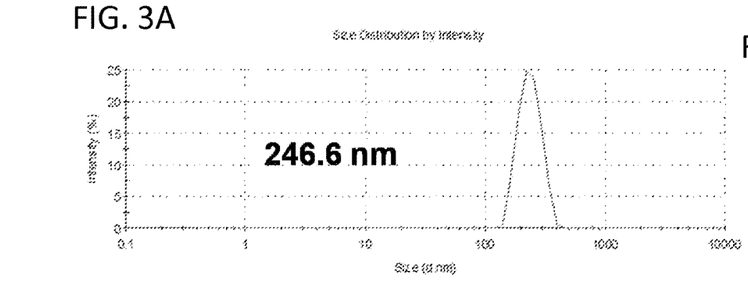
FIG. 3A is a graph illustrating the hydrodynamic size distribution of His-tagged streptavidin (H6-SA)/PLGA-Ni particles.
Figure 3B:
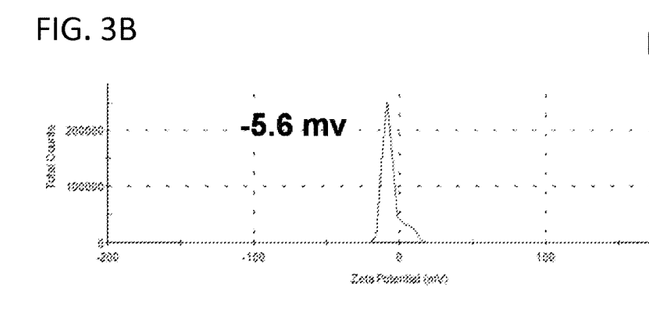
FIG. 3B is a graph illustrating the shift in zeta potential produced when PLGA-Ni particles capture H6-SA.
Figure 3C:
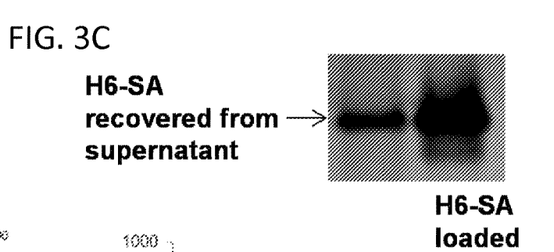
FIG. 3C is a photograph of an SDS-PAGE gel showing capture of H6-SA by PLGA-Ni particles.

Studies showed that PLGA-Ni particles could capture H6-SA (His-tagged streptavidin; Abcam, Cambridge, Mass.). Mixing PLGA-Ni particles with H6-SA resulted in particles with sizes in the submicron range (FIG. 3a; hydrodynamic radius=247 nm, polydispersity=0.1). Hydrodynamic size was determined using dynamic light scattering. Adsorption of streptavidin was evidenced by a major shift in zeta potential (FIG. 3b; −40.2→−5.6 millivolts). Suspended particles removed H6-SA from supernatant upon centrifugation (FIG. 3c). Less than 30% of protein loaded remained in the supernatant after centrifugation.

Figure 3D:
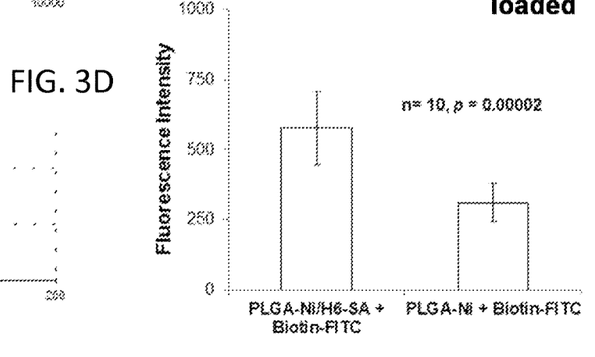
FIG. 3D is a graph illustrating increased fluorescence when PLGA-Ni/H6-SA particles were incubated with biotin-FITC compared to PLGA-Ni particles incubated with biotin-FITC.

Incubating PLGA-Ni/H6-SA with biotin-fluorescein resulted in expected surface interactions (FIG. 3d). H6-SA (50 nM) was added to particles suspended in PBS (0.1 mg/ml) and incubated for 90 min at room temperature. The particles then were incubated with biotin-FITC. After extensive washing with buffer, pellets were analyzed for fluorescence.

TFGβ can be loaded onto PLGA-Ni/ATRA using two methods. In the first, His-tagged TGFβ is incubated with PLGA-Ni/ATRA particles suspended in buffered saline at ambient temperatures. In the second method, biotinylated TGFβ (e.g., biotinylated mouse or human TGFβ, generated using NHS-biotin or commercially available from R&D Systems) is loaded onto the PLGA-Ni/ATRA/H6-SA particles. Tetravalent H6-SA bound on PLGA-Ni/ATRA allows surface loading of biotinylated TGFβ, which is generated using N-hydroxysuccinimidobiotin (NHS-biotin). Loading of TGFβ can be determined by breaking the streptavidin-biotin interaction at 70° C. (Holmberg et al., 2005). Biotinylated TGFβ (MW=44.3 kDa) can be quantified using SDS-PAGE and ELISA. In vitro release of ATRA and TGFβ can be monitored using Franz Cells to determine the time to reach 90% cumulative release ($t_{90}$) at 37° C. In this method, drug-loaded particles (1mg/ml) dissolved in PBS are placed in the donor chamber and sampling of released drugs in the receptor chamber can be done over time. A cellulose semi-permeable membrane separates the chambers.

In a study to determine TGFβ release kinetics in vitro from PLGA-Ni/ATRA/TGFβ particles, 5 mg of the particles were added to 5 mL sterile PBS with antibiotics at 37° C. with gentle shaking. Every 2 days for a period of 10 days, samples were removed and centrifuged, and TGFβ concentrations were measured by ELISA. The steady-state release rate was on average 8.2 ng/mL.

EXAMPLE 2

Treatment of Type I Diabetes

The ability of PLGA-Ni/ATRA/TGFβ particles to reverse the symptoms of diabetes in early onset NOD mice is tested. NOD mice with early onset diabetes are selected by testing blood glucose levels and identifying animals that have a blood glucose level greater than 400 mg/dL. The selected animals are given insulin pellets to normalize blood glucose levels to below 300 mg/dL. The insulin is withdrawn and treatment with PLGA-Ni/ATRA/TGFβ particles is initiated. A set (3 to 10) of animals are injected, such as twice weekly, with PLGA-Ni/ATRA/TGFβ particles. A set (3 to 10) of animals are injected with control microparticles using the same treatment protocol. After the commencement of the protocol, blood glucose levels are sampled twice weekly and animals are non-fasting during the experiment. Animals in the group that receives PLGA-Ni/ATRA/TGFβ particles show significantly lower glucose levels than the animals that receive the control treatment. Furthermore, some animals show a non-fasting blood glucose level below 300 mg/dL, typically considered to be a threshold indicator of diabetes onset.

In view of the many possible embodiments to which the principles of the disclosure may be applied, it should be recognized that the illustrated embodiments are only examples of the disclosure and should not be taken as limiting the scope of the invention. Rather, the scope of the invention is defined by the following claims. We therefore claim as our invention all that comes within the scope and spirit of these claims.

We claim:

1. A method for treating a subject with an autoimmune disorder, comprising:
    selecting a subject with the autoimmune disorder; and
    administering to the subject a therapeutically effective amount of a particle formulation comprising: a) a particle comprising all-trans retinoic acid (ATRA) encapsulated within a polymeric matrix; and b) transforming growth factor beta (TGFβ) adsorbed on a surface of the particle,
    thereby treating autoimmune disorder in the subject.

2. The method of claim 1, wherein the subject is human.

3. The method of claim 1, wherein the subject has pre-diabetes or diabetes type 1.

4. The method of claim 3, further comprising administering to the subject an additional therapy for modulating body weight or treating diabetes.

5. The method of claim 4, wherein the additional therapy comprises a lifestyle modification or insulin.

6. The method of claim 1, wherein the subject is a child.

7. The method of claim 1, wherein the subject is an adult.

8. The method of claim 1, wherein the polymeric matrix comprises poly-(d, l-lactic-co-glycolic) acid (PLGA).

9. The method of claim 1, wherein the particle further comprises a metal-chelating compound.

10. The method of claim 9, wherein the metal is nickel, zinc, copper, iron, or cobalt.

11. The method of claim 9, wherein the metal-chelating compound is a nickel-chelating lipid.

12. The method of claim 11, wherein the nickel-chelating lipid is 1,2-dioleoyl-sn-glycero-3-[(N-(5-amino-1-carboxypentyl)iminodiacetic acid)succinyl].

13. The method of claim 9, wherein (a) the TGFP is histidine-tagged TGFβ, and the histidine-tagged TGFβ is adsorbed to the particle surface via metal coordination with the histidine, or (b) the TGFβ is biotinylated, and the biotinylated TGFP is adsorbed to the particle surface via histidine-tagged streptavidin.

14. The method of claim 1, wherein the particle has a spherical morphology.

15. The method of claim 1, wherein the particle has a diameter ranging from 500 nm to 2000 nm.

* * * * *